US00RE35475E

United States Patent [19]

Kuroda et al.

[11] E Patent Number: Re. 35,475

[45] Reissued Date of Patent: Mar. 11, 1997

[54] PHOTOSENSITIVE MEMBER FOR ELECTROPHOTOGRAPHY WITH THIOPHENE CONTAINING MOIETY ON CHARGE TRANSPORT COMPOUND

[75] Inventors: Masami Kuroda; Youichi Nakamura; Noboru Furusho, all of Kawasaki, Japan

[73] Assignee: Fuji Electric Co., Ltd., Kanagawa, Japan

[21] Appl. No.: 197,599

[22] PCT Filed: Oct. 6, 1988

[86] PCT No.: PCT/JP88/01016

§ 371 Date: Jun. 6, 1989

§ 102(e) Date: Jun. 6, 1989

[87] PCT Pub. No.: WO89/03546

PCT Pub. Date: Apr. 2, 1989

Related U.S. Patent Documents

Reissue of:

[64] Patent No.: 5,089,365
Issued: Feb. 18, 1992
Appl. No.: 368,333
Filed: Jun. 6, 1989

[30] Foreign Application Priority Data

| | | | |
|---|---|---|---|
| Oct. 7, 1987 | [JP] | Japan | 62-253080 |
| Dec. 9, 1987 | [JP] | Japan | 62-311311 |
| Dec. 21, 1987 | [JP] | Japan | 62-323236 |

[51] Int. Cl.[6] ..... G03G 5/047; G03G 5/06

[52] U.S. Cl. ..... 430/59; 430/75; 430/77; 430/83

[58] Field of Search ..... 430/59, 75, 77, 430/83

[56] References Cited

U.S. PATENT DOCUMENTS

| | | | |
|---|---|---|---|
| 4,150,987 | 4/1979 | Anderson et al. | 430/59 |
| 4,353,971 | 10/1982 | Chang et al. | 430/58 |
| 4,385,106 | 5/1983 | Sakai | 430/59 |
| 4,448,868 | 5/1984 | Suzuki et al. | 430/58 |
| 4,565,761 | 1/1986 | Katagiri et al. | 430/83 |
| 4,629,670 | 12/1986 | Katagiri et al. | 430/58 |
| 4,673,630 | 6/1987 | Katagiri et al. | 430/72 |
| 4,677,045 | 6/1987 | Champ et al. | 430/76 |
| 4,839,252 | 6/1989 | Murata et al. | 430/59 |
| 4,861,691 | 8/1989 | Kuroda et al. | 430/59 |
| 4,861,692 | 8/1989 | Kuroda et al. | 430/59 |
| 4,935,323 | 6/1990 | Hattori et al. | 430/75 X |

FOREIGN PATENT DOCUMENTS

| | | | |
|---|---|---|---|
| 59-182456 | 7/1984 | Japan . | |
| 59-182457 | 7/1984 | Japan . | |
| 60-93443 | 5/1985 | Japan . | |
| 62-64055 | 11/1987 | Japan . | |
| 62-262052 | 11/1987 | Japan | 430/77 |
| 63-158560 | 7/1988 | Japan | 430/75 |

*Primary Examiner*—Roland Martin
*Attorney, Agent, or Firm*—Spencer & Frank

[57] ABSTRACT

A photosensitive member for electrophotography have a photosensitive layer 20 provided on an electroconductive substrate 1 and, containing a compound selected from among derivatives of thiophene, diphenylthiophene or oxadiazole. When the surface of the photosensitive member was positively charged and then irradiated with white light, the half decay exposure amount with which the surface potential is decreased to half is 5 to 10 lux•sec. The photosensitive member is capable of being used in semiconductor laser printers.

9 Claims, 1 Drawing Sheet

PHOTOSENSITIVE MEMBER FOR ELECTROPHOTOGRAPHY WITH THIOPHENE CONTAINING MOIETY ON CHARGE TRANSPORT COMPOUND

Matter enclosed in heavy brackets [ ] appears in the original patent but forms no part of this reissue specification; matter printed in italics indicates the additions made by reissue.

TECHNICAL FIELD

The present invention relates to a photosensitive member for electrophotography, and particularly to a photosensitive member for electrophotography comprising an electroconductive substrate and a photosensitive layer formed thereon and containing a derivative of thiophene, diphenylthiophene or oxadiazole.

BACKGROUND ART

Photosensitive materials which have heretofore been used in photosensitive members for electrophotography (hereinafter also referred to simply as "photosensitive members") include inorganic photoconductive substances such as selenium and selenium alloys, dispersions of inorganic photoconductive substances such as zinc oxide and cadmium sulfide in resin binders, organic photoconductive substances such as poly-N-vinylcarbazole and polyvinylanthracene, dispersions of organic photoconductive substances such as phthalocyanine compounds and bisazo compounds in resin binders, and films of organic photoconductive substances as mentioned above, deposited through vacuum evaporation.

Photosensitive members, which are required to have a function of retaining a surface electric charge in the dark, a function of generating an electric charge upon receiving light, and a function of transporting an electric charge upon receiving light, include so-called single layer type photosensitive members comprising one layer having all of these functions, and so-called laminate type photosensitive members with laminated layers respectively having separate functions, one layer of which mainly contributes to generation of an electric charge, and another layer of which contributes to retention of a surface electric charge in the dark and transportation of an electric charge upon receiving light. For example, a Carlson system can be applied to image formation according to the electrophotography method using one of these photosensitive members. The process of image formation according to this system comprises the step of charging a photosensitive member by corona discharge in the dark, the step of exposing the surface of the charged photosensitive member to light to form an electrostatic latent image corresponding to a letter and/or a picture on a copy or manuscript, the step of developing the formed electrostatic latent image with a toner, and the step of transferring the developed toner image to a support such as a paper sheet to fix the toner image onto the support. The photosensitive member from which the toner image was transferred to the support is subjected to removal of the electric charge, removal of the remaining toner, and removal of the electric with light to be ready for reuse.

Photosensitive members for electrophotography wherein use is made of an organic material have recently been put into practical use by virtue of flexibility, thermal stability and a film forming capacity of the organic material. Such photosensitive members include a photosensitive member comprising poly-N-vinylcarbazole and 2, 4, 7-trinitrofluoren-9-on (disclosed in U.S. Pat. No. 3,484,237), a photosensitive member comprising an organic pigment as the main component (disclosed in Japanese Patent Application Laid-Open No. 37,543/1972), and a photosensitive member comprising as the main component a eutectic complex composed of a dye and a resin (disclosed in Japanese Patent Application Laid-Open No. 10,785/1972). Further, a large number of photosensitive members wherein use is made of a hydrazone compound, an oxazole compound, or the like have been reported.

As described above, organic materials have many advantages with which inorganic materials are not endowed. However, the fact has been that there have been available no organic materials sufficiently satisfying all the characteristics required of photosensitive members for electrophotography, among which photosensitivity and characteristics in repeated continuals use have been particularly problematic.

DISCLOSURE OF THE INVENTION

The present invention has been made in view of the above-mentioned problems. An object of the present invention is to provide a photosensitive member for electrophotography to be used in a copying machine as well as a printer wherein a novel organic material which has never been used to date is used as a charge transporting substance in the photosensitive layer thereof to provide a high photosensitivity and excellent characteristics in repeated use.

In the first aspect of the present invention, a photosensitive member for electrophotography comprises:

A photosensitive layer containing at least one compound selected from among derivatives of thiophene represented by the following general formula (I):

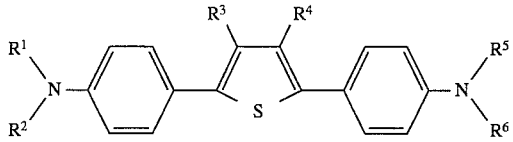

(I)

wherein R1, R2, R3, R4, R5 and R6 each stand for a substituted or unsubstituted alkyl, aryl, or aralkyl group.

Here, the photosensitive layer may be a layer made of a dispersion of a charge transporting substance and a charge generating substance in a resin binder, and wherein the charge transporting substance is at least one compound selected from among the derivatives of thiophene represented by the general formula (I).

The photosensitive layer may have laminated layers, one of which is a charge generating layer, and another of which is a charge transporting layer containing a charge transporting substance; and wherein the charge transporting substance is at least one compound selected from among the derivatives of thiophene represented by the general formula (I).

A covering layer may be provided on the laminated layers.

In the second aspect of the present invention, a photosensitive member for electrophotography comprises:

a photosensitive layer containing at least one compound selected from among derivatives of diphenylthiophene represented by the following general formula (II) or (III):

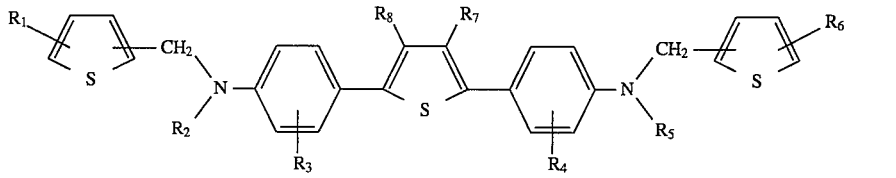

(II)

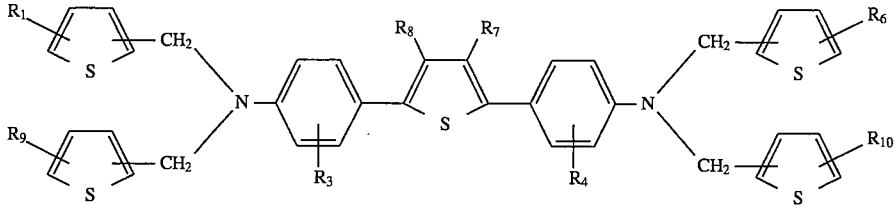

(III)

wherein R1, R2, R3, R4, R5, R6, R7, R8, R9, and R10 each stand for a hydrogen atom, a halogen atom, an alkyl group, a hydroxy group, an alkoxy group, an allyl group, a nitro group, a substituted or unsubstituted aryl group, or an aralkyl group.

Here, the photosensitive layer may be a layer made of a dispersion of a charge transporting substance and a charge generating substance in a resin binder, and wherein the charge transporting substance is at least one compound selected from among the derivatives of diphenylthiophene represented by the general formula (II) and (II).

The photosensitive layer may have laminated layers, one of which is a charge generating layer, and another of which is a charge transporting layer containing a charge transporting substance; and wherein the charge transporting substance is at least one compound selected from among the derivatives of diphenylthiophene represented by the general formula (I) or (III)

A covering layer may be provided on the laminated layers.

In the third aspect of the present invention, a photosensitive member for electrophotography, comprises:

a photosensitive layer containing at least one compound selected from among derivatives of oxidiazole represented by the following general formula (IV) or (V):

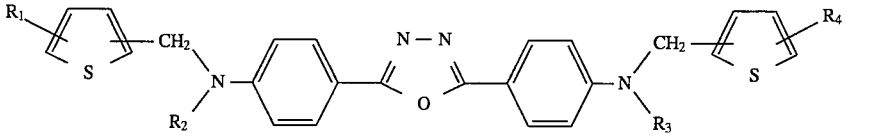

(IV)

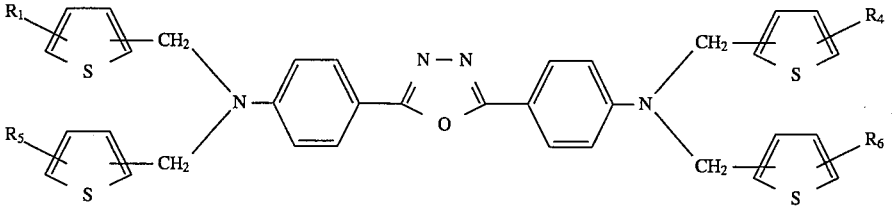

(V)

wherein R1, R2, R3, R4, R5, and R6 each stand for a hydrogen atom, a halogen atom, an alkyl group, an allyl group, a nitro group, an arakyl group, or a substituted or unsubstituted aryl group or an aralkyl group.

Here, the photosensitive layer may be a layer made of a dispersion of a charge transporting substance and a charge generating substance in a resin binder, and wherein the charge transporting substance is at least one compound selected from among the derivatives of oxadiazole represented by the general formula (IV) or (V).

The photosensitive layer may have laminated layers, one of which is a charge generating layer, and another of which is a charge transporting layer containing a charge transporting substance; and wherein the charge transporting substance is at least one compound selected from among the derivatives of oxadiazole represented by the general formula (IV) or (V).

A covering layer may be provided on the laminated layers.

BEST MODE FOR CARRYING OUT THE INVENTION

Figure 1:
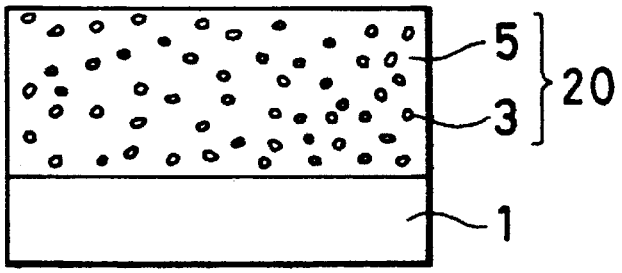
FIGS. 1 to 3 are schematic cross-sectional views of photosensitive members for electrophotography according to the present invention.
Figure 2:
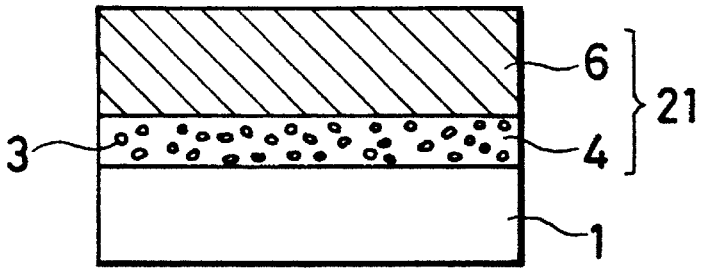
Figure 3:
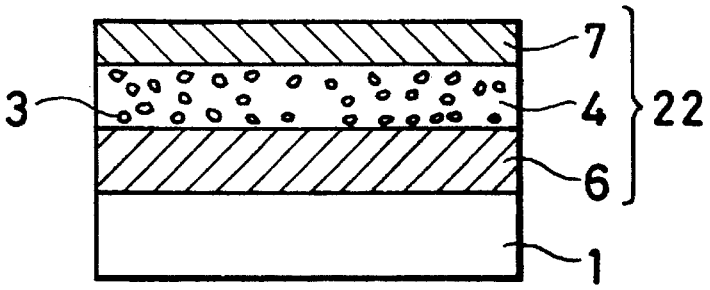

The photosensitive member of the present invention, which contains in the photosensitive layer thereof a derivative of thiophene, diphenylthiophene, or oxadiazole, may have any one of structures as respectively shown in FIGS. 1, 2 and 3 according to the manner of application thereto of the derivative of compound as mentioned above.

FIGS. 1 to 3 are schematic cross-sectional views of photosensitive members according to the present invention. In the figures, reference numeral 1 refers to an electroconductive substrate, numerals 20, 21 and 22 each to a photosensitive layer, reference numeral 3 to a charge generating substance, reference numeral 4 to a charge generating layer, reference numeral 5 to a resin layer containing a charge transporting substance, reference numeral 6 to a charge transporting layer, and reference numeral 7 to a covering layer.

FIG. 1 shows a structure (structure usually called a single layer type photosensitive member) comprising an electroconductive substrate 1 and a photosensitive layer 20 provided thereon and containing a charge generating substance a dispersed in a matrix 5 composed of a resin binder and a derivative of thiophene, diphenylthiophene or oxadiazole as a charge transporting substance.

FIG. 2 shows a structure (structure usually called a laminate type photosensitive member) comprising an electroconductive substrate 1 and a photosensitive layer 21 provided thereon in the form of laminated layers, the lower one of which is a charge generating layer 4 mainly comprising a charge generating substance 3, and the upper one of which is a charge transporting layer 6 containing a derivative of thiophene, diphenylthiophene or oxadiazole as a charge transporting substance.

FIG. 3 shows a layer structure reverse to that of FIG. 2. In this case, a covering layer 7 is generally provided to protect a charge generating layer 4.

Why two kinds of layer structures as respectively shown in FIGS. 2 and 3 provided is as follows. Even if the layer structure of FIG. 2 which is usually used according to the negatively charging mode is to be used according to the positively charging mode, no charge transporting substances adapted for the latter mode have been found. Accordingly, the layer structure of FIG. 3 as already proposed is necessary as a photosensitive member operable according to the positively charging mode at the present stage of art.

A photosensitive member as shown in FIG. 1 can be prepared by a procedure comprising the step of dispersing a charge generating substance in a solution of a charge transporting substance and a resin binder and the step of applying the resulting dispersion on an electroconductive substrate.

A photosensitive member as shown in FIG. 2 can be prepared by a procedure comprising the step of depositing a charge generating substance on an electroconductive substrate through vacuum evaporation or applying on an electroconductive substrate a dispersion prepared by dispersing particles of a charge generating substance in a solvent and a resin binder and drying the resulting coating film, and the step of applying on the deposited film or on the dried coating film a solution of a charge transporting substance and a resin binder and drying the resulting coating film.

A photosensitive member as shown in FIG. 3 can be prepared by a procedure comprising the step of applying on an electroconductive substrate a solution of a charge transporting substance and a resin binder and drying the resulting coating film, the step of depositing a charge generating substance on the dried coating film through vacuum evaporation or applying on the dried coating film a dispersion prepared by dispersing particles of a charge generating substance in a solvent and a resin binder and drying the resulting coating film, and the step of forming a covering layer.

The electroconductive substrate 1 serves not only as an electrode of the photosensitive member but also as a support for the layer(s) provided thereon. The photosensitive member may be in any form selected from a cylinder, a plate and a film, and may be made of any one of various materials including metals such as aluminum, stainless steel and nickel; and glass, resins, and the like subjected thereon to a treatment capable of rendering the same electroconductive.

The charge generating layer 4, which is formed by application of a dispersion of particles of a charge generating substance 3 in a resin binder or deposition of a charge generating substance 3 through vacuum evaporation, generated an electric charge upon receiving light. It is important that the charge generating layer 4 be high not only in efficiency of electric charge generation but also in capability of injecting a generated electric charge into the charge transporting layer 6 and the covering layer 7, which capability is desired to be little dependent upon electric field and to be high even in low electric fields. Examples of usable charge generating substances include phthalocyanine compounds such as metal-free phthalocyanine and titanylphthalocyanine; various azo, quinone and indigo pigments; dyes such as cyanine, squalilium, azulenium and pyrylium compounds; and selenium and selenium compounds. From among them, a suitable substance can be selected according to the wavelength range of a light source to be used in light exposure for image formation. Since the charge generating layer will suffice if only it has a function of generating an electric charge, the thickness thereof is determined depending on the extinction coefficient of a charge generating substance used therein. In general, the thickness of the charge generating layer is 5 μm or smaller, preferably 1 μm or smaller. It also is possible to additionally use a charge transporting substance and the like in the charge generating layer in addition to a charge generating substance as the main component of the layer. Examples of usable resin binders include polycarbonates, polyesters, polyamides, polyurethanes, epoxy resins, silicone resins, and homopolymers and copolymers of methacryric esters, which may be used either alone or in suitable combination.

The charge transporting layer 6, which is a coating film or a dispersion of a derivative of thiophene, diphenylthiophene or oxadiazole as an organic charge transporting substance in a resin binder, exhibits a function of serving as an insulating layer in the dark to retain an electric charge of the photosensitive member as well as a function of transporting an electric charge injected from the charge generating layer upon receiving light. Examples of usable binders include polycarbonates, polyesters, polyamides, polyurethanes, epoxy resins, silicone resins, and homopolymers and copolymers of methacryric esters.

The covering layer 7 has a function of receiving and retaining in the dark an electric charge generated by corona discharge and a capacity of transmitting therethrough a light to which the charge generating layer is sensitive. The covering layer 7 is required not only to transmit a light therethrough at the time of light exposure to allow the light to reach the charge generating layer but also to undergo injection of a generated electric charge to neutralize and erase a surface electric charge therewith. Usable materials of the covering layer include organic insulating film-forming materials such as polyesters and polyamides; and mixtures of organic materials as mentioned just above with an inorganic materials such as a glass resin and/or $SiO_2$ and/or with an electric resistance reducing materials such as a metal and/or a metallic oxide. However, usable materials of the covering layer are not restricted to those organic insulating film forming materials. For example, the covering layer may be formed from an inorganic or metallic material such as $SiO_2$, a metal, or a metallic oxide through vacuum evaporation and deposition, sputtering, or the like. In view of the above description, the material of the covering layer is desired to be as transparent as possible in the wavelength range wherein the maximum light absorption of a charge generating substance is attained.

The thickness of the covering layer can be arbitrarily set within the range wherein it does not bring about any adverse effects such as an increase in the residual potential when repeated continuous use is made of the photosensitive member, though it depends on the blending composition of the covering layer.
Specific examples of derivatives of thiophene which can be used in the present invention are as follows.
| COMPOUND |
|---|
| 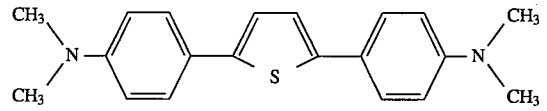 No. I-1 |
| 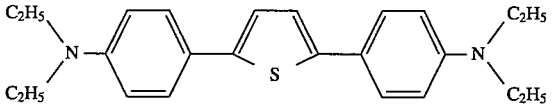 No. I-2 |
| 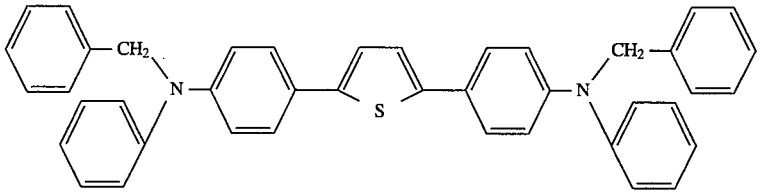 No. I-3 |
| 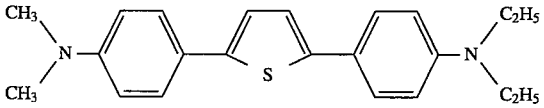 No. I-4 |
| 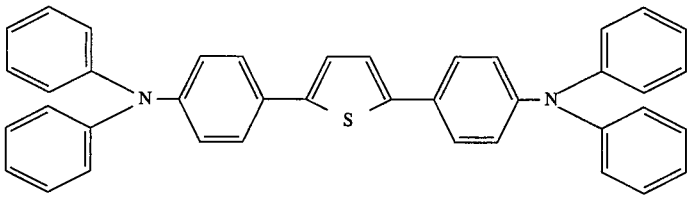 No. I-5 |
| 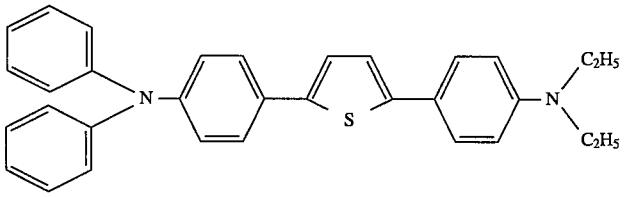 No. I-6 |
| 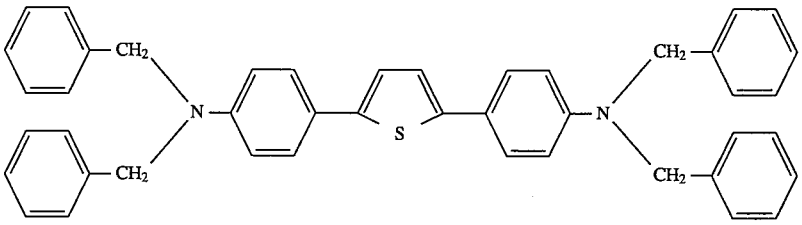 No. I-7 |
| 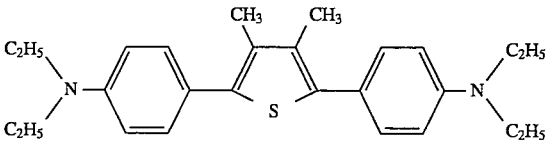 No. I-8 |
| 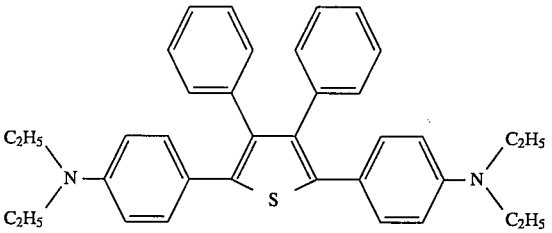 No. I-9 |

-continued
| COMPOUND |
|---|
| 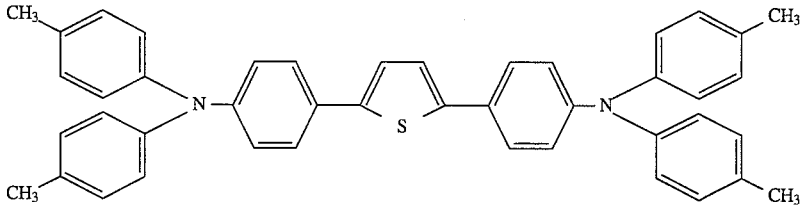 No. I-10 |
| 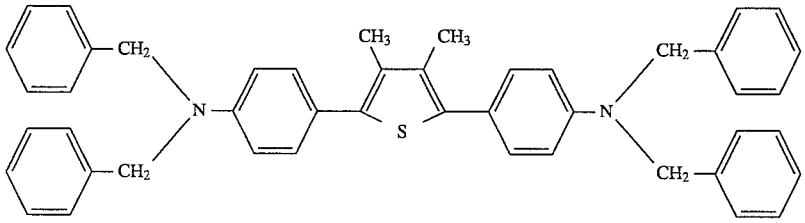 No. I-11 |
| 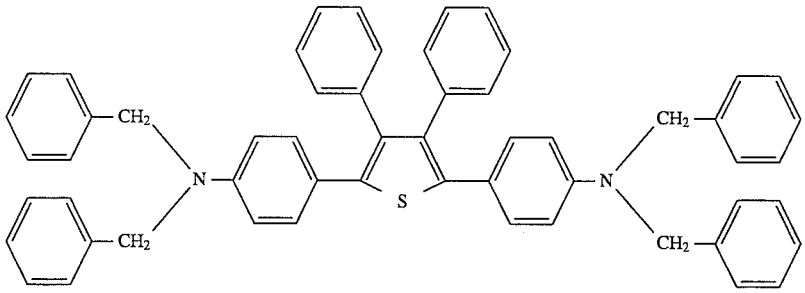 No. I-12 |
| 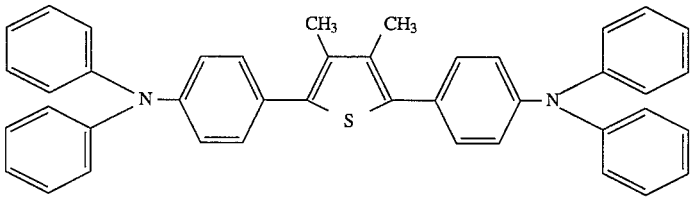 No. I-13 |
| 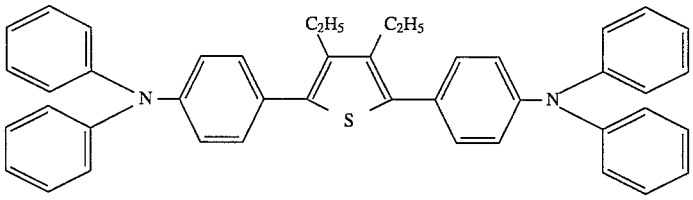 No. I-14 |
Specific examples of derivatives of diphenylthiophene which can be used in the present invention are as follows.
| COMPOUND |
|---|
| 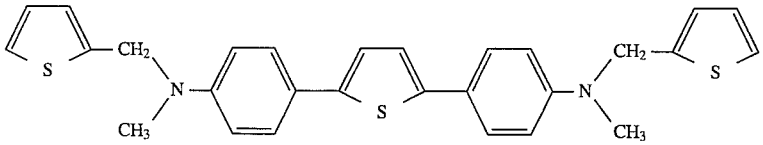 No. II-1 |
| 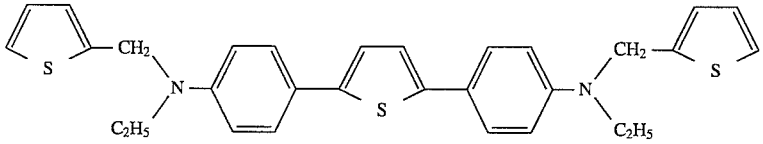 No. II-2 |

-continued
| COMPOUND | |
|---|---|
| No. II-3 | 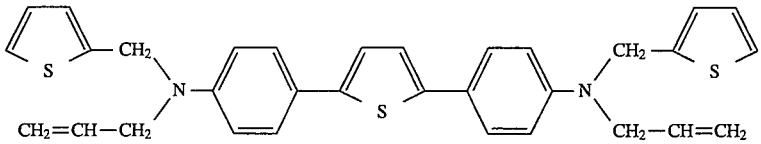 |
| No. II-4 | 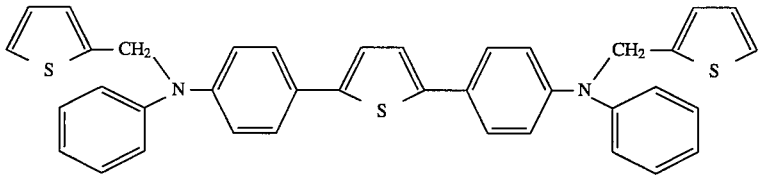 |
| No. II-5 | 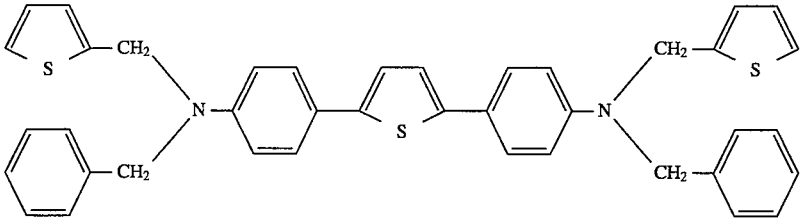 |
| No. II-6 | 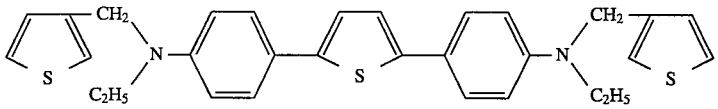 |
| No. II-7 | 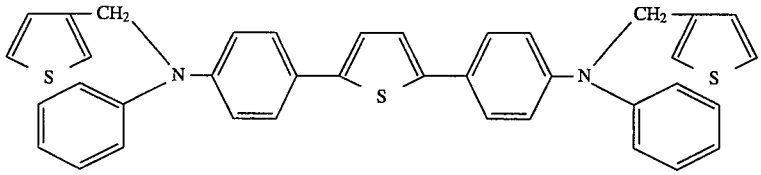 |
| No. II-8 | 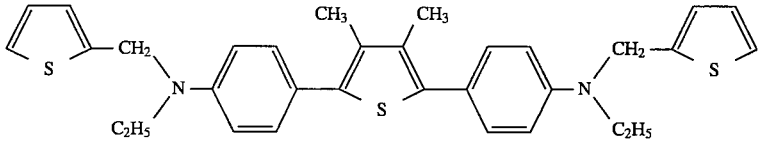 |
| No. II-9 | 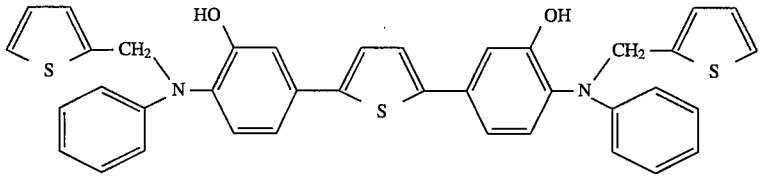 |
| No. II-10 | 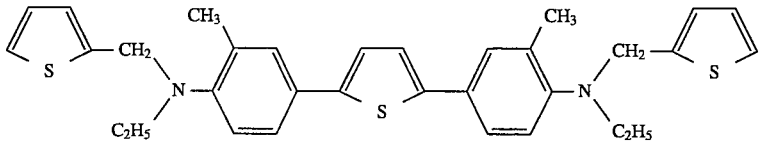 |
| No. II-11 | 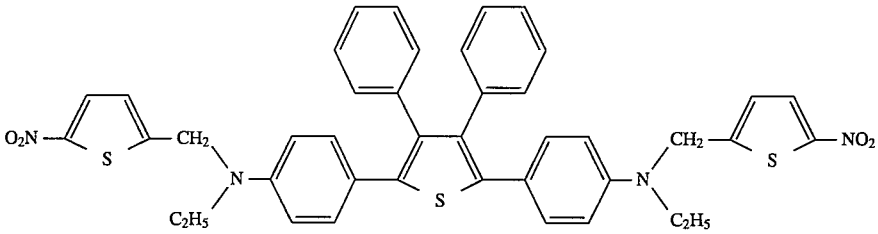 |

-continued

| COMPOUND |
|---|
| No. II-12 |
| No. II-13 |
| No. II-14 |
| No. II-15 |
| No. II-16 |
| No. II-17 |
| No. II-18 |
| No. II-19 |
| No. II-20 |

-continued

| COMPOUND |
|---|
| No. II-21 |
| No. III-1 |
| No. III-2 |
| No. III-3 |
| No. III-4 |
| No. III-5 |
| No. III-6 |

-continued
| | COMPOUND |
|---|---|
| 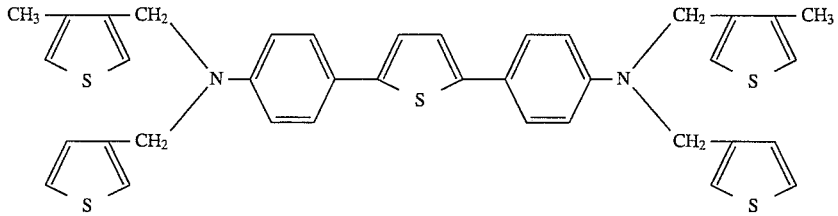 | No. III-7 |
| 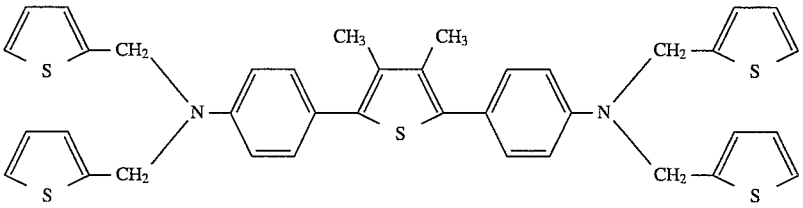 | No. III-8 |
| 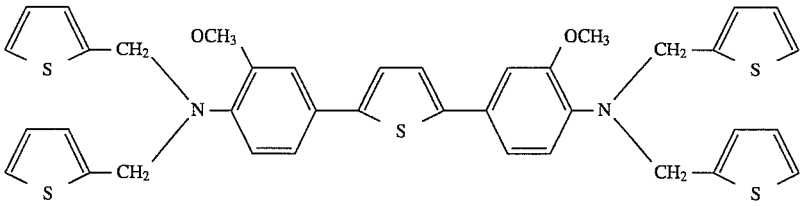 | No. III-9 |
| 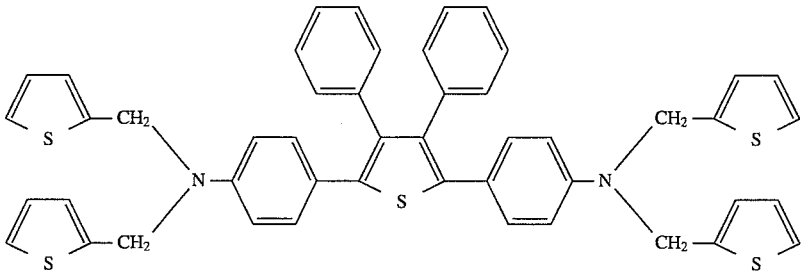 | No. III-10 |
| 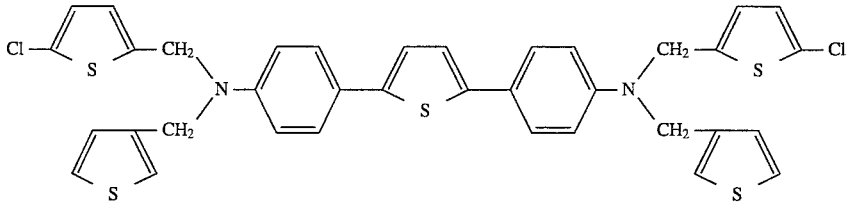 | No. III-11 |
| 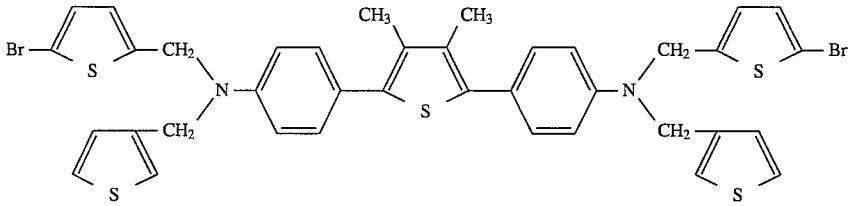 | No. III-12 |
| 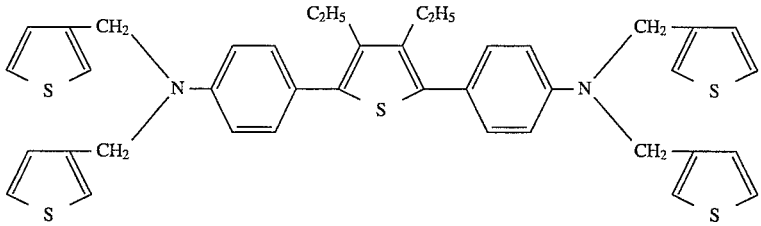 | No. III-13 |

-continued
| COMPOUND | |
|---|---|
| 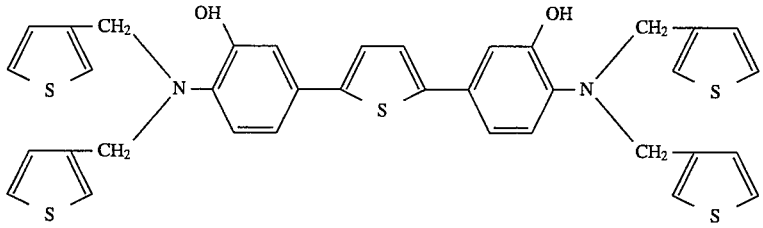 | No. III-14 |
Specific examples of derivatives of oxadiazole which can be used in the present invention are as follows.
| COMPOUND | |
|---|---|
| 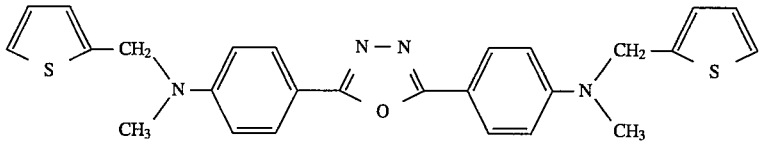 | No. IV-1 |
| 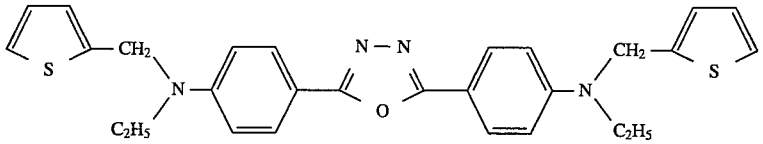 | No. IV-2 |
| 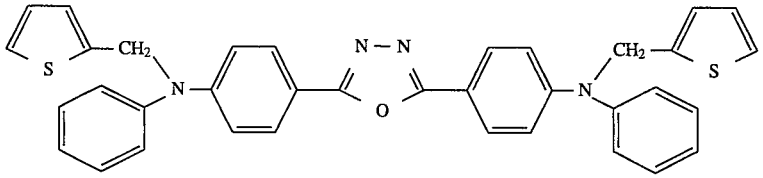 | No. IV-3 |
| 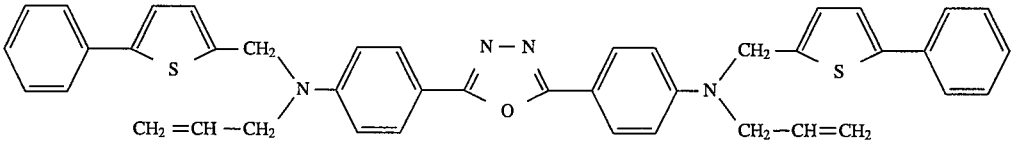 | No. IV-4 |
| 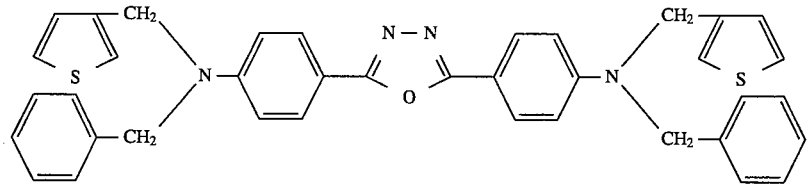 | No. IV-5 |
| 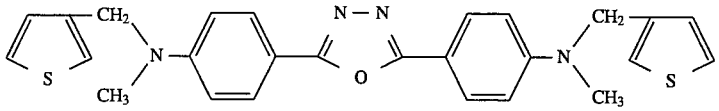 | No. IV-6 |
| 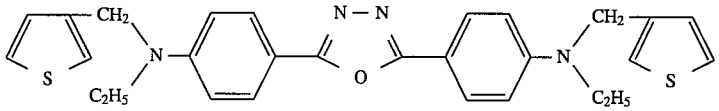 | No. IV-7 |

-continued
| COMPOUND | |
|---|---|
| No. IV-8 | 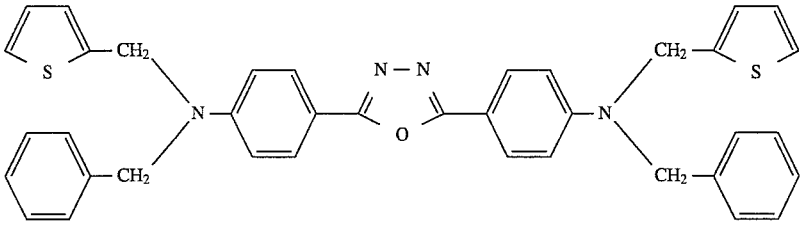 |
| No. IV-9 | 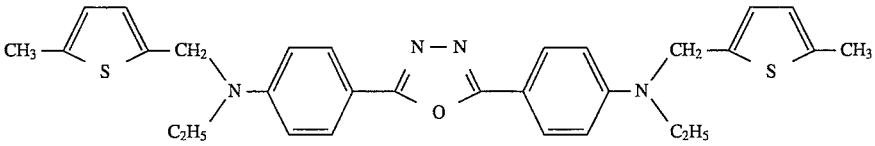 |
| No. IV-10 | 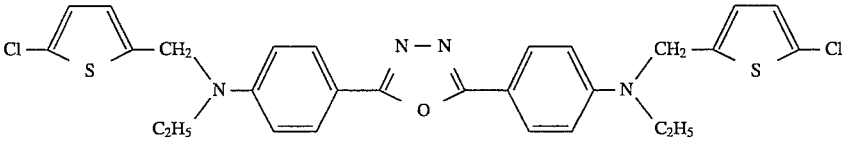 |
| No. V-1 | 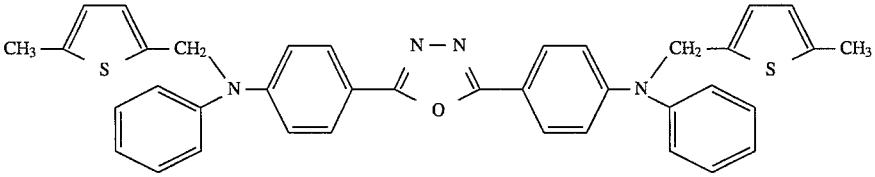 |
| No. V-2 | 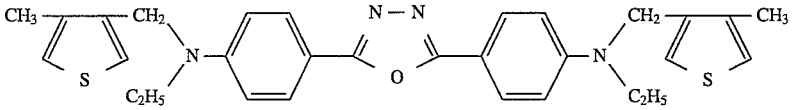 |
| No. V-3 | 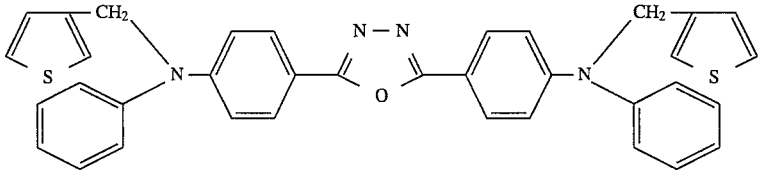 |
| No. V-4 | 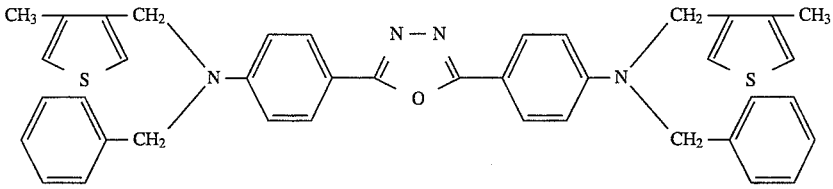 |
| No. V-5 | 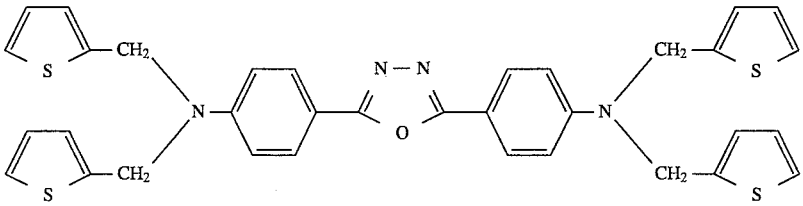 |
| No. V-6 | 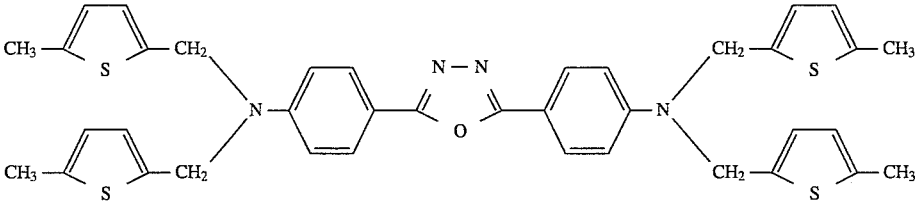 |

-continued

| COMPOUND | |
|---|---|
| 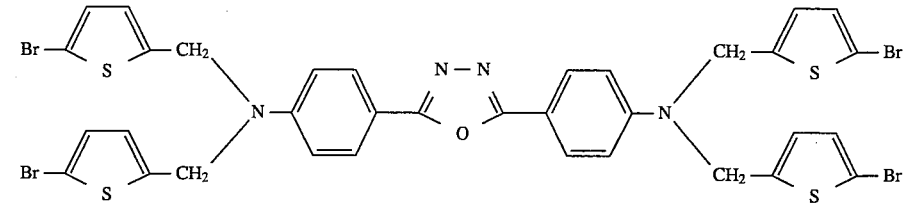 | No. V-7 |
| 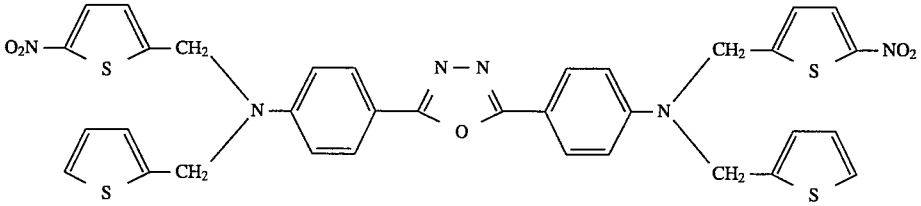 | No. V-8 |
| 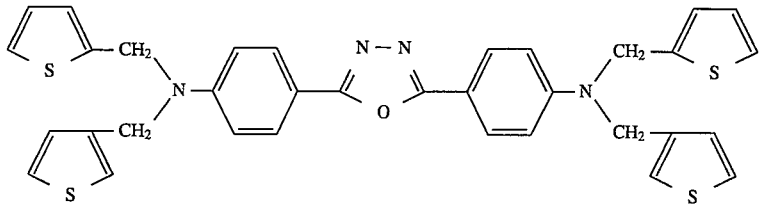 | No. V-9 |
| 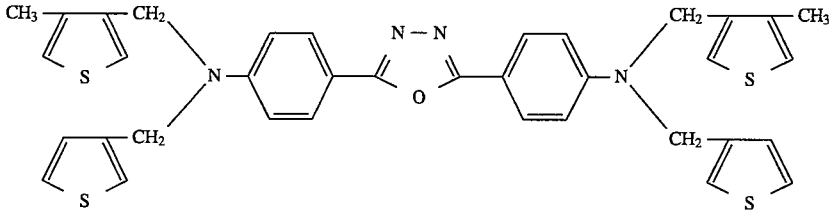 | No. V-10 |
| 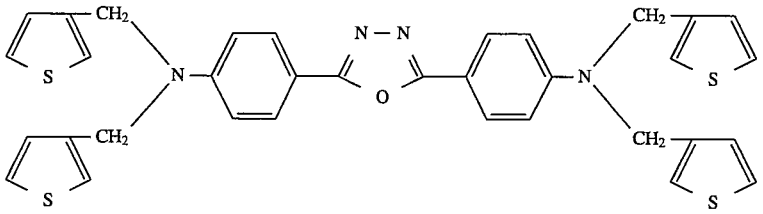 | No. V-11 |

Examples will now be given, wherein the compounds Nos. I-1 to I-14 were respectively used.

EXAMPLE I-1

50 parts by weight of metal-free phthalocyanine (manufactured by Tokyo Kasei Co., Ltd.) pulverized with a ball mill for 150 hours and 100 parts by weight of the compound No. I-1, a derivative of thiophene, were kneaded, with a mixer, together with 100 parts by weight of a polyester resin (trademark: Vylon 200, manufactured by Toyobo Co., Ltd.) and tetrahydrofuran (THF) as a solvent for 3 hours to prepare a coating liquid. The coating liquid was applied on an aluminum-deposited polyester film (Al-PET) as an electroconductive substrate by the wire bar technique to form a photosensitive layer having a dry thickness of 15 μm. Thus, a photosensitive member having a structure as shown in FIG. 1 was produced.

EXAMPLES I-2

First, metal-free α-phthalocyanine as a starting material was pulverized for 20 minutes into a fine powder with a pulverizer, a LIMMAC (Linear Induction Motor Mixing and Crushing manufactured by Fuji Electric Co., Ltd.) wherein a non-magnetic can containing the metal-free α-phthalocyanine and Teflon pieces as small acting pieces was placed between two linear motors faced each other. 1 part by weight of this fine powder sample and 50 parts of DMF (N, N-dimethylformamide) as a solvent were subjected to an ultrasonic dispersion treatment. Thereafter, the sample was separated from DMF by filtration and dried to completer the treatment of metal-free phthalocyanine.

Subsequently, a solution of 100 parts by weight of the compound No. I-2, a derivative of thiophene, in 700 parts by weight of tetrahydrofuran (THF) was mixed with a solution of 100 parts by weight of polymethyl methacrylate (PMMA; manufactured by Tokyo Kasei Co., Ltd.) in 700 parts by weight of toluene to prepare a coating liquid, which was then applied on an aluminum-deposited polyester film substrate by the wire bar technique to form a charge transporting layer having a dry thickness of 15 μm. 50 parts by weight of the metal-free phthalocyanine treated in the-above-mentioned manner, 50 parts by weight of a polyester resin (trademark: Vylon 200), and 50 parts by weight of PMMA were kneaded together with THF as a solvent with a mixer for 3 hours to prepare a coating liquid, which was then applied on the charge transporting layer by the wire bar technique to form a charge generating layer having a dry thickness of 1 μm. Thus, a photosensitive member having a structure corresponding to that of FIG. 3 was produced. No covering layer was provided because it is not directly relevant to the present invention.

EXAMPLE I-3

A photosensitive member was produced by forming a photosensitive layer in substantially the same manner as in Example I-1 except that 50 parts by weight of metal-free phthalocyanine, 100 parts by weight of the compound No. I-3, a derivative of thiophene, 50 parts by weight of a polyester resin (trademark: Vylon 200), and 50 parts by weight of PMMA were used to replace therewith the composition of the photosensitive layer of Example I-1.

EXAMPLE I-4

A photosensitive member was produced by forming a photosensitive layer in substantially the same manner as in Example I-3 except that Chlorodiane Blue which is a bisazo pigment disclosed in, for example, Japanese Patent Application Laid-Open No. 37,543/1972 was used instead of metal-free phthalocyanine.

The four photosensitive member thus produced were examined with respect to the electrophotographic characteristics thereof by using an electrostatic recording paper testing apparatus (Kawaguchi Denki Model SP-428).

The surface potential Vs (volts) of a photosensitive member is an initial surface potential of the photosensitive member when the surface thereof was positively charged in the dark by corona discharge at +6.0 kV for 10 seconds. Subsequently, the photosensitive member was kept in the dark for 2 seconds after the discontinuation of corona discharge followed by a measurement of the surface potential Vd (volts) thereof. Immediately thereafter, the surface of the photosensitive member was irradiated with white light at an illuminance of 2 luxes to find a time (seconds) required till the surface potential thereof was decreased to half of the value of Vd, from which time and the illuminance the half decay exposure amount E½ (lux•second) was calculated. The surface potential of the photosensitive member measured just after the surface thereof was irradiated with white light at an illuminance of 2 luxes for 10 seconds is defined as the residual potential Vr (volts) thereof. Where a phthalocyanine compound was used as the charge generating substance, a monochromatic light having a wavelength of 780 nm was also used to measure the electrophotographic characteristics of a photosensitive member since the photosensitive member had been expected to show a high sensitive even to a long wavelength light. Specifically, the same procedure as mentioned above was repeated up to the measurement of Vd, but thereafter the surface of the photosensitive member was irradiated with a monochromatic light (wavelength: 780 nm) of 1 μW instead of the white light to find the half decay exposure amount (μJ/cm$^2$) thereof as well as to measure the residual potential Vr (volts) just after 10 seconds of irradiation with the monochromatic light.

The results of the measurements are shown in Table 1.

TABLE 1

| | White Light | | | Light with Wavelength of 780 nm | | |
|---|---|---|---|---|---|---|
| Example No. | Vs (volts) | Vr (volts) | E½ (lux · sec) | Vs (volts) | Vr (volts) | E½ (μJ/cm$^2$) |
| I-1 | 650 | 40 | 4.8 | 600 | 70 | 4.2 |
| I-2 | 780 | 60 | 5.5 | 750 | 90 | 4.9 |
| I-3 | 750 | 50 | 5.1 | 780 | 90 | 4.1 |
| I-4 | 800 | 50 | 4.9 | — | — | — |

As can be seen in Table 1, the photosensitive members of Examples I-1, I-2, I-3 and I-4 were not substantially different therebetween in half decay exposure amount and residual potential, and showed good surface potential characteristics. The photosensitive members of Examples I-1 I-2 and I-3, using a phthalocyanine compound as the charge generating substance, showed excellent electrophotographic characteristics for a light with a long wavelength of 780 nm as well.

Example I-5

Selenium was deposited on an aluminum plate having a thickness of 500 μm through vacuum evaporation to form a charge generating layer having a thickness of 1.5 μm. A solution of 100 parts by weight of the compound No. I-4, a derivative of thiophene, in 700 parts by weight of tetrahydrofuran (THF) was mixed with a solution of 100 parts by weight of polymethylmethacrylate (PMMA; manufactured by Tokyo Kasei Co., Ltd.) in 700 parts by weight of toluene to prepare a coating liquid, which was then applied on the charge generating layer by the wire bar technique to form a charge transporting layer having a dry thickness of 20 μm. Thus, a photosensitive member having the structure shown in FIG. 2 was produced. This photosensitive member was charged by corona discharge at −6.0 kV for 0.2 second and examined with respect to electrophotographic characteristics to obtain good results, namely Vs=−680 V, Vr=−50 V, and E½=4.5 lux•sec.

EXAMPLE I-6

50 parts by weight of metal-free phthalocyanine treated in the same manner as in Example I-1, 50 parts by weight of a polyester resin (trademark: Vylon 200), and 50 parts by eight of PMMA were kneaded together with THF as a solvent with a mixer for 3 hours to prepare a coating liquid, which was then applied on an aluminum support to form a charge generating layer having a thickness of about 1 μm. 100 parts by weight of the compound No. I-5, a derivative of thiophene, 100 parts by weight of a polycarbonate resin (Panlite L-1250; manufactured by Teijin Kasei Co., Ltd.), and 0.1 part of a silicone oil were mixed with 700 parts by weight of THF and 700 parts by weight of toluene to prepare a coating liquid, which was then applied on the charge generating layer to form a charge transporting layer having a thickness of about 15 μm.

The photosensitive member thus obtained was charged by corona discharge at −6.0 kV for 0.2 second and examined with respect to electrophotographic characteristics in the same manner as in Example I-5 to obtain good results, namely Vs=−720 V and E½=6.1 lux•sec.

EXAMPLE I-7

Photosensitive members were produced by forming respective photosensitive layers in substantially the same manner as in Example I-4 except the that the compounds Nos. I-6 to I-14 were respectively used instead of the compound No. I-4. The results obtained by using the electrostatic recording paper testing apparatus (SP-428) are shown in Table 2. Table 2 shows the half decay exposure amounts E½ (lux•sec) obtained under the experimental conditions where the photoconductors were positively charged in the dark by corona discharge at +6.0 kV for 10 seconds and irradiated with white light at an illuminance of 2 luxes.

TABLE 2

| Compound No. | E½(lux · sec) |
|---|---|
| I-7 | 5.1 |
| I-8 | 4.9 |
| I-9 | 5.5 |
| I-10 | 4.4 |
| I-11 | 5.8 |
| I-12 | 4.3 |
| I-13 | 4.2 |
| I-14 | 4.6 |

As can be seen in Table 2, the photosensitive members using the respective compounds Nos. I-6 to I-14, derivatives of thiophene, were satisfactory with respect to half decay exposure amount E½, namely sensitivity.

Examples will now be given, wherein the compounds Nos. II-1 to II-21 and III-1 to III-12 were respectively used to produce photosensitive members.

EXAMPLE II-1

A photosensitive member having the structure shown in FIG. 1 and comprising a photosensitive layer having a thickness of 15 μm was produced in substantially the same manners in Example I-1 except that the compound No. II-1, a derivative of diphenylthiophene, was used instead of the compound No. I-1.

EXAMPLE II-2

A photosensitive member having a structure corresponding to that of FIG. 3 but having no covering layer was produced in substantially the same manner as in Example I-2 except that the compound No. II-2, a derivative of diphenylthiophene, was used instead of the compound No. I-2. The thickness of the charge transporting layer of the member was 15 μm, while the thickness of the charge generating layer was 1 μm.

EXAMPLE II-3

A photosensitive member was produced by forming a photosensitive layer in substantially the same manner as in Example II-1 except that 50 parts by weight of metal-free phthalocyanine, 100 parts by weight of the compound No. II-3, a derivative of diphenylthiophene, 50 parts by weight of a polyester resin (trademark: Vylon 200), and 50 parts by weight of PMMA were used to replace therewith the composition of the photosensitive layer of Example II-1.

EXAMPLE II-4

A photosensitive member was produced by forming a photosensitive layer in substantially the same manner as in Example II-3 except that Chlorodiane Blue which is a bisazo pigment disclosed in, for example, Japanese Patent Application Laid-Open No. 37,543/1972 was used instead of metal-free phthalocyanine.

The four photosensitive member thus produced were examined with respect to surface potential Vs, residual potential Vr, and half decay pressure amount E½ by using while light as well as a monochromatic light (wavelength: 780 nm) in the same manner as in Examples I-1 to I-4. The results of the measurements are shown in Table 3.

TABLE 3

| | White Light | | | Light with Wavelength of 780 nm | | |
|---|---|---|---|---|---|---|
| Example No. | Vs (volts) | Vr (volts) | E½ (lux · sec) | Vs (volts) | Vr (volts) | E½ (μJ/cm²) |
| II-1 | 600 | 50 | 6.8 | 620 | 50 | 6.2 |
| II-2 | 720 | 70 | 7.1 | 730 | 60 | 6.9 |
| II-3 | 700 | 60 | 6.1 | 720 | 60 | 5.6 |
| II-4 | 680 | 80 | 5.9 | — | — | — |

As can be seen in Table 3, the photosensitive members of Examples II-1, II-2, II-3 and II-4 were comparable to one another in half decay exposure amount and residual potential, and showed good surface potential characteristics. The photosensitive members of Examples II-1, II-2 and II-3, using a phthalocyanine compound as the charge generating substance, showed a high sensitivity to a light with a long wavelength of 780 nm as well, thus proving that they are sufficiently capable of being used in semiconductor laser printers.

EXAMPLE II-5

A photosensitive member with the structure shown in FIG. 2 was produced by forming a charge generating layer having a thickness of 15 μm and a charge transporting layer having a dry thickness of 20 μm in substantially the same manner as in Example I-5 except that the compound No. II-4, a derivative of diphenylthiophene, was used instead of the compound No. I-4. This photosensitive member was charged by corona discharge at −6.0 kV for 0.2 second and examined with respect to electrophotographic characteristics to obtain good results, namely Vs=−670 V, Vr=−60 V, and E½=5.5 lux•sec.

EXAMPLE II-6

A charge generating layer having a thickness of about 1 μm was formed on an aluminum support in the same manner as in Example I-6. Subsequently, a charge transporting layer having a thickness of about 15 μm was formed on the charge generating layer in substantially the same manner as in Example I-6 except that the compound No. II-5, a derivative of diphenylthiophene, was used instead of the compound No. I-5.

The photosensitive member thus obtained was charged by corona discharge at −6.0 kV for 0.2 second and examined with respect to electrophotographic characteristics in the same manner as in Example II-4 to obtain good results, namely Vs=−620 V and E½=6.5 lux•sec.

EXAMPLE II-7

Photosensitive members were produced by forming respective photosensitive layers in substantially the same manner as in Example II-4 except that the compounds Nos. II-6, to II-21 and III-1 to III-14 were respectively used instead of the compound No. II-3, and were examined with respect to half decay exposure amount by using the electrostatic recording paper testing apparatus (Kawaguchi Denki Model SP-428). The results are shown in Table 4, in which the half decay exposure amounts E½ (lux•sec) are values in the case where the members were positively charged in the dark by corona discharge at +6.0 kV for 10 seconds and irradiated with white light at an illuminance of 2 luxes.

TABLE 4

| Compound No. | E½(lux · sec) |
|---|---|
| II-6 | 6.5 |
| II-7 | 7.2 |
| II-8 | 6.1 |
| II-9 | 6.7 |
| II-10 | 5.7 |
| II-11 | 7.2 |
| II-12 | 6.8 |
| II-13 | 5.6 |
| II-14 | 6.3 |
| II-15 | 7.7 |
| II-16 | 7.8 |
| II-17 | 6.2 |
| II-18 | 7.8 |
| II-19 | 7.9 |
| II-20 | 7.3 |
| II-21 | 7.9 |
| III-1 | 7.2 |
| III-2 | 7.1 |
| III-3 | 8.9 |
| III-4 | 8.5 |
| III-5 | 8.8 |
| III-6 | 7.4 |
| III-7 | 9.6 |
| III-8 | 6.5 |
| III-9 | 6.9 |
| III-10 | 6.9 |
| III-11 | 4.7 |
| III-12 | 6.3 |
| III-13 | 7.0 |
| III-14 | 8.9 |

As can be seen in Table 4, the photosensitive members using the respective compounds Nos. II-6 to II-21 and III-1 to III-14, derivatives of diphenylthiophene, as charge transporting substances were satisfactory with respect to half decay exposure amount E½.

Examples will now be given, wherein the compounds Nos. IV-1 to IV-10 and V-1 to V-11 were respectively used to produce photosensitive members.

EXAMPLE III-1

A photosensitive member having the structure shown in FIG. I and comprising a photosensitive layer having a thickness of 15 μm was produced in substantially the same manner as in Example I-1 except that the compound No. IV-1, a derivative of oxadiazole, was used instead of the compound No. I-1.

EXAMPLE III-2

A photosensitive member having a structure corresponding to that of FIG. 3 but having no covering layer was produced in substantially the same manner as in Example I-2 except that the compound No. IV-2, a derivative of oxadiazole, was used instead of the compound No. I-2. The thickness of the charge transporting layer of the member was 15 μm, while the thickness of the charge generating layer was 1 μm.

EXAMPLE III-3

A photosensitive member was produced by forming a photosensitive layer in substantially the same manner as in Example III-1 except that 50 parts by weight of the metal-free phthalocyanine, 100 parts by weight of the compound No. IV3, a derivative of oxadiazole, 50 parts by weight of a polyester resin (trademark: Vylon 200), and 50 parts by weight of PMMA were used to replace therewith the composition of the photosensitive layer of Example III-1.

EXAMPLE III-4

A photosensitive member was produced by forming a photosensitive layer in substantially the same manner as in Example III-3 except that Chlorodiane Blue which is a Bisazo pigment disclosed in, for example, Japanese Patent Application Laid-Open No. 37,543/1972 was used instead of metal-free phthalocyanine.

The four photosensitive members thus produced were examined with respect to surface potential Vs, residual potential Vr, and half decay exposure amount E½ by using white light as well as a monochromatic light (wavelength: 780 nm) in the same manner as in Examples I-1 to I-4. The results of the measurements are shown in Table 5.

TABLE 5

| | White Light | | | Light with Wavelength of 780 nm | | |
|---|---|---|---|---|---|---|
| Example No. | Vs (volts) | Vr (volts) | E½ (lux · sec) | Vs (volts) | Vr (volts) | E½ (μJ/cm²) |
| III-1 | 640 | 60 | 5.6 | 650 | 30 | 4.8 |
| III-2 | 650 | 80 | 6.0 | 660 | 50 | 5.2 |
| III-3 | 680 | 60 | 5.8 | 650 | 40 | 5.7 |
| III-4 | 660 | 70 | 6.6 | — | — | — |

As can be seen in Table 5, the photosensitive members of Examples III-1, III-2, III-3 and III-4 were comparable to one another in half decay exposure amount and residual potential, and showed good surface potential characteristics. The photosensitive members of Examples III-1, III-2 and III-3, using a phthalocyanine compound as the charge generating substance, showed a high sensitivity to alight with a long wavelength of 780 nm as well, thus proving that they are sufficiently capable of being used in semiconductor layer printers.

EXAMPLE III-5

A photosensitive member having the structure shown in FIG. 2 was produced by forming a charge generating layer having a thickness of 1.5 μm and a charge transporting layer having a dry thickness of 20 μm in substantially the same manner as in Example I-5 except that the compound No. IV-4, a derivative of oxadiazole, was used instead of the compound No. I-4. This photosensitive member was charged by corona discharge at −6.0 kV for 0.2 second and examined with respect to electrophotographic characteristics to obtain good results, namely Vs=−600 V, Vr=−50 V, and E½=4.8 lux•sec.

EXAMPLE III-6

A charge generating layer having a thickness of about 1 82 m was formed on an aluminum support in the same manner as in Example I-6. Subsequently, a charge transporting layer having a thickness of about 15 μm was formed on the charge generating layer in substantially the same manner as in Example I-6 except that the compound No. IV-5, a derivative of oxadiazole, was used instead of then compound No. I-5.

The photosensitive member thus obtained was charged by corona discharge at −6.0 kV for 0.1 second and examined with respect to electrophotographic characteristics in the same manner as in Example III-5 to obtain good results, namely Vs=−640 V and E½=5.5 lux•sec.

EXAMPLE III-7

Photosensitive members were produced by forming respective photosensitive layers in substantially the same manner as in Example III-4 except that the compounds Nos. IV-6 to IV-10 and V-1 to V-11 were respectively used instead of the compound No. III-3, and were examined with respect to half decay exposure amount by using the electrostatic recording paper testing apparatus (Kawaguchi Denki Model SP-428). The results are shown in Table 6, in which the half decay exposure amounts E½ (lux•sec) are values in the case where the members were positively charged in the dark by corona discharge at +6.0 kV for 10 seconds and irradiated with white light at an illuminance of 2 luxes.

TABLE 6

| Compound No. | E½(lux · sec) |
|---|---|
| IV-6 | 6.9 |
| IV-7 | 7.0 |
| IV-8 | 6.6 |
| IV-9 | 8.2 |
| IV-10 | 5.4 |
| V-1 | 7.6 |
| V-2 | 5.9 |
| V-3 | 6.1 |
| V-4 | 7.8 |
| V-5 | 6.7 |
| V-6 | 7.5 |
| V-7 | 8.4 |
| V-8 | 5.9 |
| V-9 | 6.0 |
| V-10 | 7.5 |
| V-11 | 6.7 |

As can be seen in Table 6, the photosensitive members using the respective compounds Nos. IV-6 to IV-10 and V-1 to V-11, derivatives of oxadiazole, as charge transporting substances were satisfactory with respect to half decay exposure mount E½.

INDUSTRIAL APPLICABILITY

According to the present invention, the use, on an electroconductive substrate, of a derivative of thiophene, diphenylthiophene or oxadiazole as a charge transporting substance can provide a photosensitive member showing a high sensitivity and excellent characteristics in repeated use when adapted for either a positively charging mode or a negatively charging mode. A suitable charge generating substance can be chosen so as to be adapted to the kind of light source to be used for exposure of a photosensitive member to light. By way of example, a phtnalocyanine compound or bisazo compound of a certain kind can be used as the charge generating substance to provide a photosensitive member capable of being used in semiconductor laser printers. If necessary, a covering layer may be provided on the surface of a photosensitive member to improve the durability thereof.

We claim:

[1. A photosensitive member for electrophotography, comprising:

an electroconductive substrate; and a photosensitive layer formed on said electroconductive substrate and containing a charge generating substance and a charge transporting substance, said charge transporting substance being at least one compound selected from among derivatives of thiophene represented by the following general formula (I):

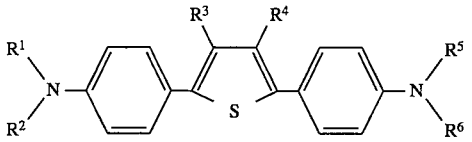

(I)

wherein R1, R2, R3, R4, R5 and R6 each stand for a substituted or unsubstituted alkyl, aryl, or aralkyl group.]

[2. The photosensitive member for electrophotography as claimed in claim 1, wherein said photosensitive layer is a single layer made of a dispersion of said charge transporting substance and said charge generating substance in a resin binder.]

[3. The photosensitive member for electrophotography as claimed in claim 1, wherein said photosensitive layer has laminated layers, one of which is a charge generating layer containing said charge generating substance and another of which is a charge transporting layer containing said charge transporting substance.]

[4. The photosensitive member for electrophotography as claimed in claim 3, further comprising a covering layer provided on said laminated layers.]

5. A photosensitive member for electrophotography, comprising:

an electroconductive substrate; and a photosensitive layer formed on said electroconductive substrate and containing a charge generating substance and a charge transporting substance, said charge transporting substance being at least one compound selected from among derivatives of diphenylthiophene represented by the following general formula (II) or (III):

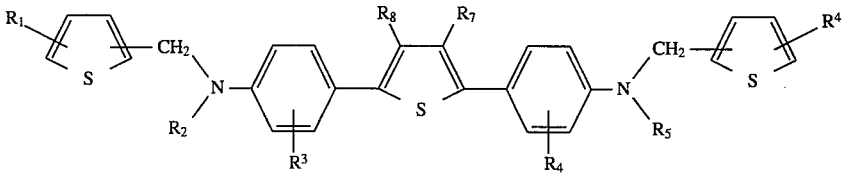

(II)

-continued

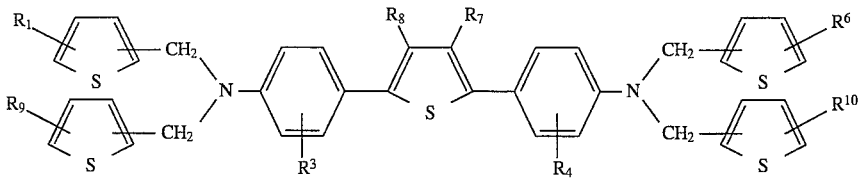

(III)

wherein R1, R2, R3, R4, R5, R6, R7, R8, R9, and R10 each stand for a hydrogen atom, a halogen atom, an alkyl group, a hydroxy group, an alkoxy group, an allyl group, nitro group, a substituted or unsubstituted aryl group, or an aralkyl group.

6. The photosensitive member for electrophotography as claimed in claim 5, wherein said photosensitive layer is a single layer made of a dispersion of said charge transporting substance and said charge generating substance in a resin binder.

7. The photosensitive member for electrophotography as claimed in claim 5, wherein said photosensitive layer has laminated layer, one of which is a charge generating layer containing said charge generating substance, and another of which is a charge transporting layer containing said charge transporting substance.

8. The photosensitive member for electrophotography as claimed in claim 7, further comprising a covering layer provided on said laminated layers.

9. A photosensitive member for electrophotography, comprising:

an electroconductive substrate; and a photosensitive layer formed on said electroconductive substrate and containing a charge generating substance and a charge transporting substance, said charge transporting substance being at least one compound selected from among derivatives of oxadiazole represented by the following general formula (IV) or (V):

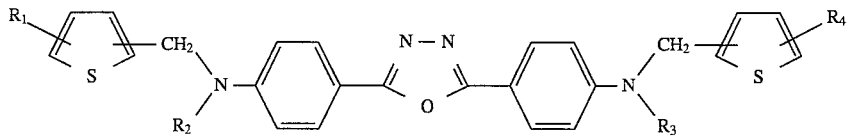

(IV)

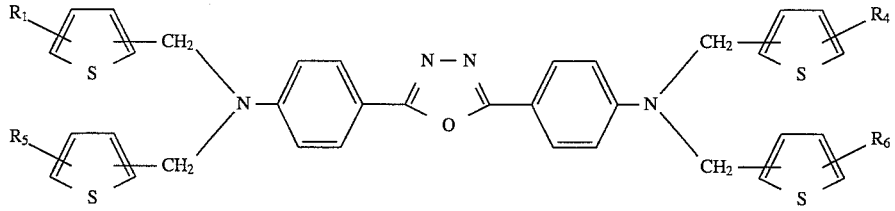

(V)

wherein R1, R2, R3, R4, R5, and R6 each stand for a hydrogen atom, a halogen atom, an alkyl group, an allyl group, a nitro group, an aralkyl group, or a substituted or unsubstituted aryl group or an aralkyl group.

10. The photosensitive member for electrophotography as claimed in claim 9, wherein said photosensitive layer is a layer made of a dispersion of said charge transporting substance and said charge generating substance in a resin binder.

11. The photosensitive member for electrophotography as claimed in claim 9, wherein said photosensitive layer has laminated layers, one of which is a charge generating layer containing said charge generating substance, and another of which is a charge transporting layer containing said charge transporting substance.

12. The photosensitive member for electrophotography as claimed in claim 11, further comprising a covering layer provided on said laminated layers.

*13. A photosensitive member for electrophotography, comprising:*

*an electroconductive substrate; and photosensitive layer formed on said electroconductive substrate and containing a charge generating substance and a charge transporting substance, said charge transporting substance being at least one thiophene derivative selected from the group consisting of thiophene derivatives having a formula:*

*(I)*

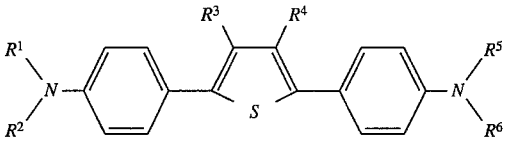

*wherein $R_1$, $R_2$, $R_3$, $R_4$, $R_5$ and $R_6$ each represents a substituted or unsubstituted alkyl, aryl or aralkyl group,*

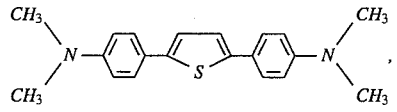

*(I-1)*

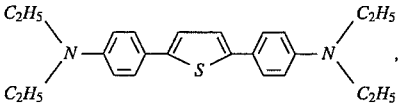

*(I-2)*

-continued
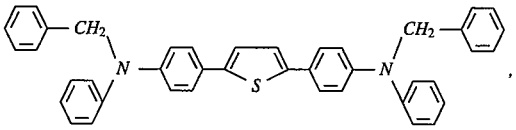
(I-3)
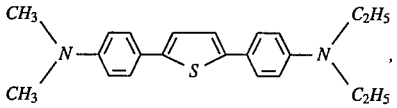
(I-4)
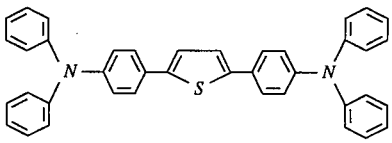
(I-5)
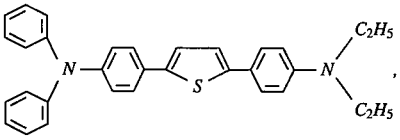
(I-6)
-continued
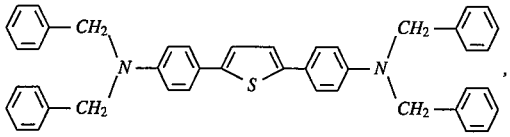
(I-7)
*and*
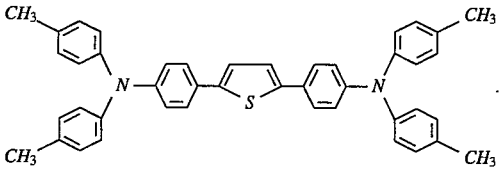
(I-10)
* * * * *

UNITED STATES PATENT AND TRADEMARK OFFICE

CERTIFICATE OF CORRECTION

PATENT NO. : Re. 35,475

DATED : March 11, 1997

INVENTOR(S) : Masami Kuroda et al.

It is certified that error appears in the above-identified patent and that said Letters Patent is hereby corrected as shown below:

**On the title page, item [*] Notice:"The portion of the term of this patent subsequent to December 22, 2007 has been disclaimed" to --The portion of the term of this patent subsequent to August 29, 2006 has been disclaimed--.**

Signed and Sealed this

Tenth Day of March, 1998

*Attest:*

*Attesting Officer*

BRUCE LEHMAN

*Commissioner of Patents and Trademarks*